US012611122B2

(12) United States Patent
Philippine et al.

(10) Patent No.: US 12,611,122 B2
(45) Date of Patent: *Apr. 28, 2026

(54) ELECTRICALLY-ISOLATED AND MOISTURE-RESISTANT DESIGNS FOR WEARABLE DEVICES

(71) Applicant: Dexcom, Inc., SAn Diego, CA (US)

(72) Inventors: Mandy Philippine, San Carlos, CA (US); Scott Matula, Alameda, CA (US); Johan Vanderhaegen, Cupertino, CA (US); Louis Jung, Foster City, CA (US); Nivi Arumugam, San Francisco, CA (US)

(73) Assignees: DexCom, Inc., San Diego, CA (US); Verily Life Sciences LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/737,150

(22) Filed: Jun. 7, 2024

(65) Prior Publication Data

US 2024/0398288 A1 Dec. 5, 2024

Related U.S. Application Data

(63) Continuation of application No. 16/930,837, filed on Jul. 16, 2020, now Pat. No. 12,029,553, which is a
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/1486* (2013.01); *A61B 5/14865* (2013.01);
(Continued)

(58) Field of Classification Search
CPC ........... A61B 5/00; A61B 5/0031; A61B 5/01; A61B 5/021; A61B 5/022; A61B 5/024;
(Continued)

(56) References Cited

U.S. PATENT DOCUMENTS 6,144,869 A 11/2000 Berner et al.
6,764,446 B2 7/2004 Wolinsky et al.
(Continued)

OTHER PUBLICATIONS

"Chapter 12: Printed Circuit Board (PCB) Design Issues", Analog Devices, Available Online at: http://www.analog.com/library/analogdialogue/archives/43-09/edch%2012%20pc%20issues.pdf, 2012, 97 pages.
(Continued)

*Primary Examiner* — Timothy J. Dole
(74) *Attorney, Agent, or Firm* — Snell & Wilmer LLP

(57) ABSTRACT

An example continuous glucose monitor includes a printed circuit board ("PCB") having first and second outer layers and an inner layer; a semiconductor package having a plurality of pins coupled to the first outer layer of the PCB; an electrical contact formed on the second outer layer of the PCB; a trace having a first portion disposed on the first outer layer, a second portion disposed on the inner layer, and a third portion disposed on the second outer layer, the trace having a first end coupled to a first pin of the plurality of pins and a second end coupled to the electrical contact; and an encapsulant disposed around a perimeter of the semiconductor package, the encapsulant covering the plurality of pins, the first portion of the sensor trace, the third portion of the sensor trace, wherein an upper surface of the semiconductor package remains exposed.

12 Claims, 6 Drawing Sheets

Related U.S. Application Data continuation of application No. 16/224,887, filed on Dec. 19, 2018, now Pat. No. 10,736,549, which is a continuation of application No. 15/964,227, filed on Apr. 27, 2018, now Pat. No. 10,182,750.

(60) Provisional application No. 62/490,970, filed on Apr. 27, 2017.

(51) Int. Cl.

| | | |
|---|---|---|
| *A61B 5/1486* | (2006.01) | |
| *A61B 5/157* | (2006.01) | |
| *H05K 3/28* | (2006.01) | |

(52) U.S. Cl.
CPC ............ *A61B 5/157* (2013.01); *A61B 5/6801* (2013.01); *H05K 3/284* (2013.01); *A61B 2562/166* (2013.01)

(58) Field of Classification Search
CPC .. A61B 5/03; A61B 5/076; A61B 5/30; A61B 5/72; A61B 5/145; A61B 5/157; A61B 5/742; A61B 5/1451; A61B 5/1486; A61B 5/6801; A61B 5/6833; A61B 5/6849; A61B 5/7203; A61B 5/7275; A61B 5/7475; A61B 5/14503; A61B 5/14532; A61B 5/14546; A61B 5/14865; H05K 1/02; H05K 1/028; H05K 1/167; H05K 1/182; H05K 3/284; G06F 1/163; G06F 1/1616; G06F 1/1626; G06F 1/1635; G06F 1/1643; G06F 1/1652; G06F 1/1656; G06F 1/1684; H01L 21/44; H01L 23/34; H01L 23/36; H01L 23/48
USPC ........ 600/347, 309, 373, 561; 361/302, 688, 361/750, 751; 428/201, 213, 411.1, 702; 607/2, 9, 61, 63, 116; 257/48, 741; 307/104; 333/176, 182
See application file for complete search history.

(56) References Cited

U.S. PATENT DOCUMENTS

| | | | |
|---|---|---|---|
| 8,465,425 B2 | 6/2013 | Heller et al. | |
| 8,579,853 B2 | 11/2013 | Reggiardo et al. | |
| 9,243,276 B2 | 1/2016 | Malecha | |
| 9,402,570 B2 | 8/2016 | Pace et al. | |
| 9,635,761 B2 | 4/2017 | Brigham et al. | |
| 9,865,575 B2 | 1/2018 | Chi et al. | |
| 9,980,669 B2 | 5/2018 | Cole et al. | |
| 10,182,750 B1 * | 1/2019 | Philippine ............ A61B 5/6801 |
| 10,736,549 B1 | 8/2020 | Philippine et al. | |
| 2004/0167801 A1 | 8/2004 | Say et al. | |
| 2005/0016844 A1 | 1/2005 | Burke et al. | |
| 2007/0149897 A1 | 6/2007 | Ghesquiere et al. | |
| 2009/0093687 A1 | 4/2009 | Telfort et al. | |
| 2009/0321930 A1 | 12/2009 | Marcoux | |
| 2010/0137778 A1 | 6/2010 | Kunjan et al. | |
| 2010/0324392 A1 | 12/2010 | Yee et al. | |
| 2011/0213225 A1 | 9/2011 | Bernstein et al. | |
| 2012/0092812 A1 | 4/2012 | Lewis et al. | |
| 2012/0266251 A1 | 10/2012 | Birtwhistle et al. | |
| 2014/0008110 A1 | 1/2014 | Arnold et al. | |
| 2014/0163338 A1 * | 6/2014 | Roesicke ............ A61B 5/0031 600/309 |
| 2014/0217566 A1 * | 8/2014 | Goida ...................... H01L 23/10 257/676 |
| 2014/0254092 A1 | 9/2014 | Im et al. | |
| 2015/0004756 A1 | 1/2015 | Chi et al. | |
| 2015/0014045 A1 | 1/2015 | Brigham et al. | |
| 2015/0220109 A1 | 8/2015 | Von Badinski et al. | |
| 2015/0296622 A1 * | 10/2015 | Jiang ...................... H05K 1/028 361/749 |
| 2015/0351648 A1 * | 12/2015 | Harvey ................... A61B 5/076 600/561 |
| 2016/0013148 A1 | 1/2016 | Lin et al. | |
| 2016/0034066 A1 * | 2/2016 | Nah ...................... G06F 3/0443 345/174 |
| 2016/0162060 A1 * | 6/2016 | Hong ...................... G06F 3/041 428/411.1 |
| 2017/0027514 A1 * | 2/2017 | Biederman .......... A61B 5/1451 |
| 2017/0188898 A1 | 7/2017 | Jina et al. | |
| 2018/0075200 A1 | 3/2018 | Davis et al. | |
| 2018/0120892 A1 | 5/2018 | Von Badinski et al. | |
| 2018/0228416 A1 | 8/2018 | Frick | |
| 2019/0021636 A1 | 1/2019 | Walter | |

OTHER PUBLICATIONS

U.S. Appl. No. 15/964,227 , "Notice of Allowance", Sep. 26, 2018, 11 pages.

U.S. Appl. No. 16/224,887 , "Final Office Action", Feb. 7, 2020, 13 pages.

U.S. Appl. No. 16/224,887 , "Non-Final Office Action", Oct. 28, 2019, 15 pages.

U.S. Appl. No. 16/224,887 , "Notice of Allowance", Apr. 8, 2020, 10 pages.

U.S. Appl. No. 16/930,837 , "Advisory Action", Jan. 6, 2022, 3 pages.

U.S. Appl. No. 16/930,837 , "Final Office Action", Aug. 15, 2023, 14 pages.

U.S. Appl. No. 16/930,837 , "Final Office Action", Oct. 28, 2021, 16 pages.

U.S. Appl. No. 16/930,837 , "Final Office Action", Jul. 15, 2022, 17 pages.

U.S. Appl. No. 16/930,837 , "Non-Final Office Action", Jun. 4, 2021, 10 pages.

U.S. Appl. No. 16/930,837 , "Non-Final Office Action", Apr. 4, 2022, 14 pages.

U.S. Appl. No. 16/930,837 , "Non-Final Office Action", Feb. 9, 2023, 14 pages.

U.S. Appl. No. 16/930,837 , "Notice of Allowance", Mar. 7, 2024, 8 pages.

* cited by examiner

102

104

101

104

105

ELECTRICALLY-ISOLATED AND MOISTURE-RESISTANT DESIGNS FOR WEARABLE DEVICES

CROSS-REFERENCE TO RELATED APPLICATIONS

The present application is a continuation of U.S. patent application Ser. No. 16/930,837, filed Jul. 16, 2020, entitled "Electrically-Isolated And Moisture-Resistant Designs For Wearable Devices," which is a continuation of U.S. patent application Ser. No. 16/224,887, filed Dec. 19, 2018, now U.S. Pat. No. 10,736,549, issued Aug. 11, 2020, entitled "Electrically-Isolated And Moisture-Resistant Designs For Wearable Devices," which is a continuation of U.S. patent application Ser. No. 15/964,227, filed Apr. 27, 2018, now U.S. Pat. No. 10,182,750, issued Jan. 22, 2019, entitled "Electrically-Isolated And Moisture-Resistant Designs For Wearable Devices," which claims priority to Provisional Application No. 62/490,970, filed on Apr. 27, 2017, and entitled "Electrically-Isolated And Moisture-Resistant Designs For Wearable Devices," the entireties of each which are hereby incorporated by reference herein.

FIELD

The present application generally relates to wearable devices, but more specifically relates to electrically-isolated and moisture-resistant designs for wearable devices.

BACKGROUND

A person with diabetes generally monitors her blood glucose levels so that she can properly administer insulin at the correct times and in the correct doses. To do so, she may periodically prick a finger to draw a small quantity of blood. The blood may be inserted into a blood glucose sensing device, which measures blood glucose level and reports the value to the user. This form of blood glucose testing is frequently referred to as a "finger prick" test. An alternative to the finger prick test is to wear a continuous glucose monitor ("CGM"), which is applied to the user's body, often on the user's abdomen. The CGM includes a sensor wire that is inserted into the wearer's skin and obtains glucose levels from the wearer's interstitial fluid. The CGM is able to then communicate the glucose level to the user via an interface device, such as the user's smartphone or an insulin pump.

SUMMARY

Various examples are described for electrically-isolated and moisture-resistant designs for wearable devices. One example wearable device includes a printed circuit board ("PCB") having first and second outer layers and an inner layer, the inner layer disposed between the first and second outer layers; a semiconductor package having four corner portions and a plurality of pins, the semiconductor package coupled to the first outer layer of the PCB via the plurality of pins; an electrical ground plane formed on the PCB and coupled to at least one pin at each of a first, second, and third of the four corner portions, and not coupled to any pins at a fourth corner portion; an electrical contact for a sensor wire formed on the second outer layer of the PCB; a sensor trace having a first portion disposed on the first outer layer, a second portion disposed on the inner layer, and a third portion disposed on the second outer layer, the sensor trace having a first end coupled to a first pin of the plurality of pins and a second end coupled to the electrical contact for the sensor wire, the first pin at the fourth corner of the semiconductor package; a plurality of guard rings disposed on the PCB, each guard ring encircling one of the portions of the sensor trace; and an encapsulant disposed around a perimeter of the semiconductor package, the encapsulant covering (i) the plurality of pins, (ii) the first portion of the sensor trace, (iii) the third portion of the sensor trace, wherein an upper surface of the semiconductor package remains exposed.

Another example example wearable device includes a printed circuit board ("PCB") having first and second outer layers and an inner layer, the inner layer disposed between the first and second outer layers; a semiconductor package having four corner portions and a plurality of pins, the semiconductor package coupled to the first outer layer of the PCB via the plurality of pins; an electrical contact for a sensor wire formed on the second outer layer of the PCB; a sensor trace having a first portion disposed on the first outer layer, a second portion disposed on the inner layer, and a third portion disposed on the second outer layer, the sensor trace having a first end coupled to a first pin of the plurality of pins and a second end coupled to the electrical contact for the sensor wire, the first pin at a fourth corner portion of the semiconductor package; and an encapsulant disposed around a perimeter of the semiconductor package, the encapsulant covering (i) the plurality of pins, (ii) the first portion of the sensor trace, (iii) the third portion of the sensor trace, wherein an upper surface of the semiconductor package remains exposed.

One example for providing a wearable biosensor includes forming a wearable biosensor electronics portion by: providing a plurality of PCB layers; affixing a semiconductor package to a first layer of the PCB layers, the semiconductor package having a plurality of pins; applying a first electrical trace to the first layer, the first electrical trace having a first end coupled to a pin of the semiconductor package and a second end coupled to a first via formed in the first layer; applying a guard ring to the first PCB layer, the guard rings encircling the first electrical trace, the pin, and the first via; applying a second electrical trace to a second PCB layer of the PCB layers, the second electrical trace having a first end coupled to a sensor wire and a second end coupled to a second via formed in the second PCB layer; applying a third electrical trace on a third PCB layer of the PCB layers, the third electrical trace having a first end coupled to the first via and a second end coupled to the second via; bonding the third PCB layer between the first and second PCB layers; affixing a sensor wire to a second PCB layer, the sensor wire having a first portion extending away from the second PCB layer; applying a first encapsulant over the pins of the semiconductor package and the first electrical trace, and not applying the encapsulant to an upper surface of the semiconductor package; and applying the encapsulant over the second electrical trace; disposing the wearable biosensor electronics portion in a first portion of a housing, the first portion defining a hole to receive the first portion of the sensor wire; sealing a second portion of the housing to the first portion of the housing to enclose the wearable biosensor electronics portion; and sealing the hole using the encapsulant.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figures 1A, 1B, 1C:
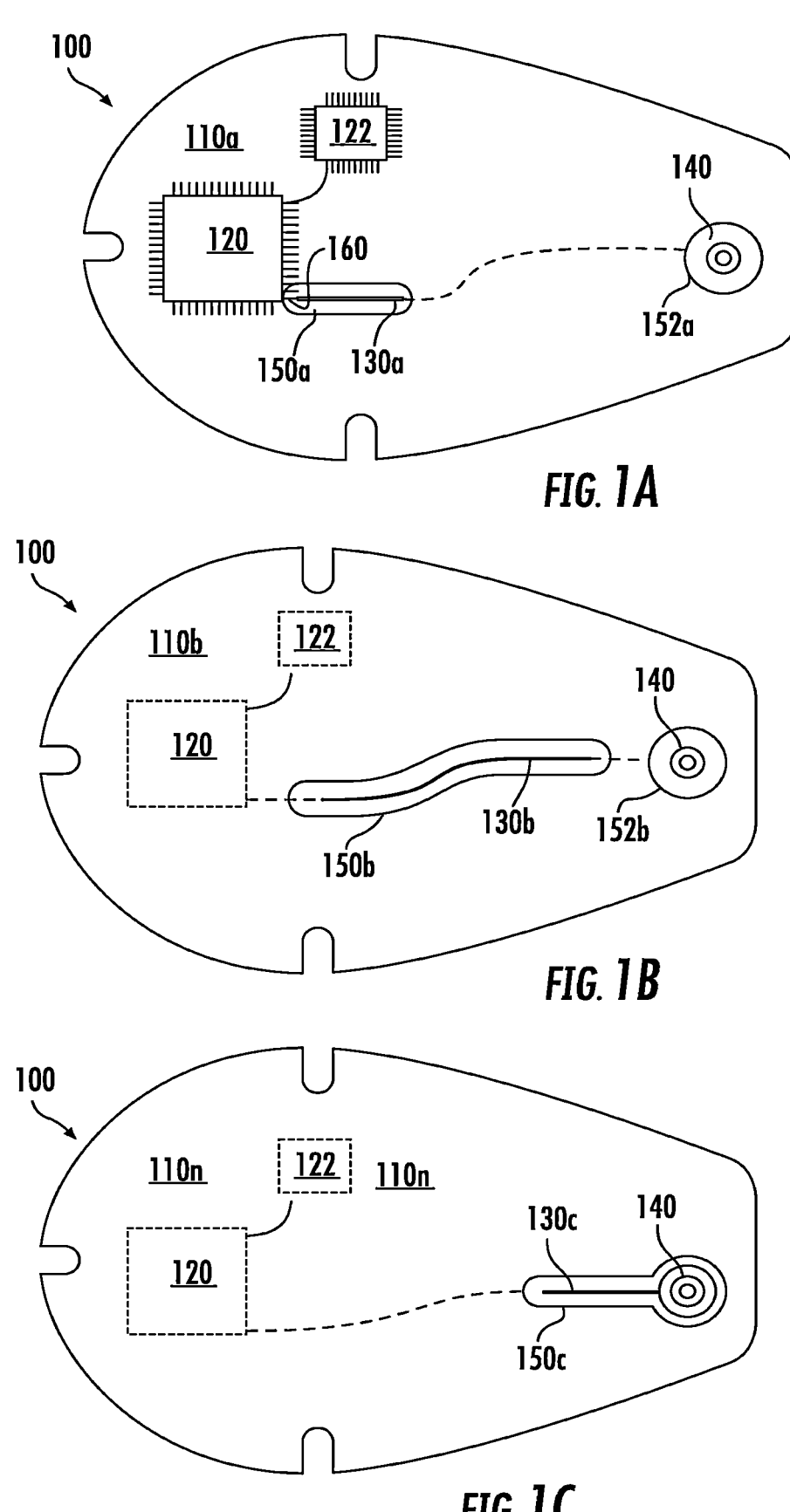
FIGS. 1A-1G show views of an example electronics portion of a CGM.

Examples are described herein in the context of electrically-isolated and moisture-resistant designs for wearable devices. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

According to one illustrative example, a CGM is designed and manufactured to provide moisture resistance to the CGM's electronics and to provide electrical isolation for the CGM's sensor lead. In this example, the CGM is designed to have a low profile to provide a more comfortable, less bulky CGM to wear. Thus, the CGM is designed to have a height of approximately 9 millimeters ("mm"), excluding the length of sensor wire that extends below the lower surface of the CGM's housing.

In addition, because the CGM is worn on the wearer's body for a number of days, and through the wearer's typical routine, it may be exposed to a wide variety of environments, including immersion in water, soap, sweat, or other moisture sources. Thus, maintaining moisture protection for the electronics within the CGM is of particular importance, while also allowing for the low profile of the CGM. Further, because the sensor electronics of the CGM are highly sensitive to extraneous electrical signals, preventing shorts due to moisture, as well as preventing leakage currents from other electronic components or traces is critical to the proper functioning of the device, properly isolating the sensor electronics, while maintaining a low profile form factor, is another key feature of the design.

As mentioned above, this example CGM has a low-profile housing that defines the overall dimensions of the CGM, excluding the external portion of the sensor wire. The housing itself defines an internal cavity in which the CGM's electronics are positioned. The electronics include an application-specific integrated circuit ("ASIC") package having a rectangular footprint, a wireless transceiver, and a sensor wire, all of which are affixed to a multi-layer printed circuit board ("PCB"). The ASIC package encases custom circuitry to receive sensor signals, determine glucose levels, and provide glucose level data to the wireless transceiver. In addition, the sensor wire is physically and electrically connected to the PCB and is connected via an electrical trace to the ASIC package, thereby enabling communication from the sensor to the ASIC.

To protect against moisture shorting pins on the ASIC package or the wireless transceiver, or from shorting other electrical connections or leads, a potting compound is applied around the perimeter of the ASIC package and wireless transceiver and overtop of the ASIC package's and transceiver package's electrical contacts, as well as the electrical trace 130a-c running from the sensor wire 140 to the ASIC package 120; however, potting compound is not applied to other portions of the CGM electronics. For example, the potting compound is not applied to the upper surfaces of the semiconductor packages or other taller electronics features coupled to the PCB, as such a placement would increase the overall height of the device. By only applying the potting compound to these portions of the CGM electronics, the total amount of volume occupied by the CGM electronics and potting compound may be reduced, thereby enabling a CGM with the desired height of less than approximately 9 mm. Such a height may be desirable to allow the CGM to remain flush against the wearer's skin and avoid unintentional contact with the wearer's limbs, clothing, or other objects.

In addition to providing moisture resistance via the potting compound, the sensor wire, which extends below a bottom surface of the CGM, is coupled to the lowest layer of the PCB, and coupled to an electrical trace, which runs from the lowest layer of the PCB to a via, where the electrical trace is routed onto an interior layer of the PCB, where it is protected from moisture by adjoining layers of the PCB. The via in this example is also filled with a potting compound to seal the via 132b running from the lowest layer to the interior layer. The electrical trace runs from the via 132b to a second via 132a located in close proximity to the contact pin on the ASIC package that accepts signals from the sensor, at which location the electrical trace traverses the second via 132a, also filled with a potting compound, to the upper surface of the PCB and connects to the ASIC package.

In addition to providing moisture resistance, electrical features are included to electrically-isolate the sensor wire from other portions of the CGM electronics to mitigate leakage current to the sensor wire, which may introduce error into signals provided by the sensor wire. The electrical features include a modified ground plane for the ASIC package and a guard ring encircling the electrical trace coupling the sensor wire to the ASIC package and the sensor wire electrical contacts themselves. In the case of a CGM, the signal provided by the sensor wire 140 is extremely small and highly susceptible to interference from leakage current. As will be discussed in more detail below, the sensor wire 140 may only provide a few nanoamps of current to indicate a glucose level. Thus, leakage current in the nanoamp range or greater can entirely overwhelm the signal provided by the sensor 140 itself.

The ground plane 180 connections for the ASIC package are provided at three corner portions of the ASIC package, but not at the fourth. In addition, the ground plane trace on the PCB associated with the ASIC package 120 is shaped to provide a gap in the ground plane 180 adjacent to the fourth corner portion, where the sensor wire electrical trace 130a connects to the ASIC package 120. By providing space for a portion of the guard ring 150a, the guard ring 150a can entirely encircle and electrically isolate the electrical trace 130a from the ground plane 180 or other electrical traces or sources of electrical leakage on the PCB. The guard ring 150*a* also encircles the portion of the sensor wire electrical trace 130*a* on the upper layer 110*a* of the PCB. The portion of the sensor wire electrical trace 130*b* running along the interior layer 110*b* of the PCB is also encircled by a guard ring 150*b*, and the portion of the sensor wire electrical trace 130*c* running along the lowest layer 110*n* of the PCB to the sensor wire connection itself is encircled by a guard ring 150*c*. Thus, the entire lengths of the different portions of the sensor wire electrical trace 130*a-c* are electrically isolated by their respective guard rings.

Such features enable a low-profile CGM, while providing sufficient moisture resistance and an electrically-isolated sensor to reduce error in sensor readings. This illustrative example is given to introduce the reader to the general subject matter discussed herein and the disclosure is not limited to this example. The following sections describe various additional non-limiting examples and examples of electrically-isolated and moisture-resistant designs for wearable devices.

Figure 1D:
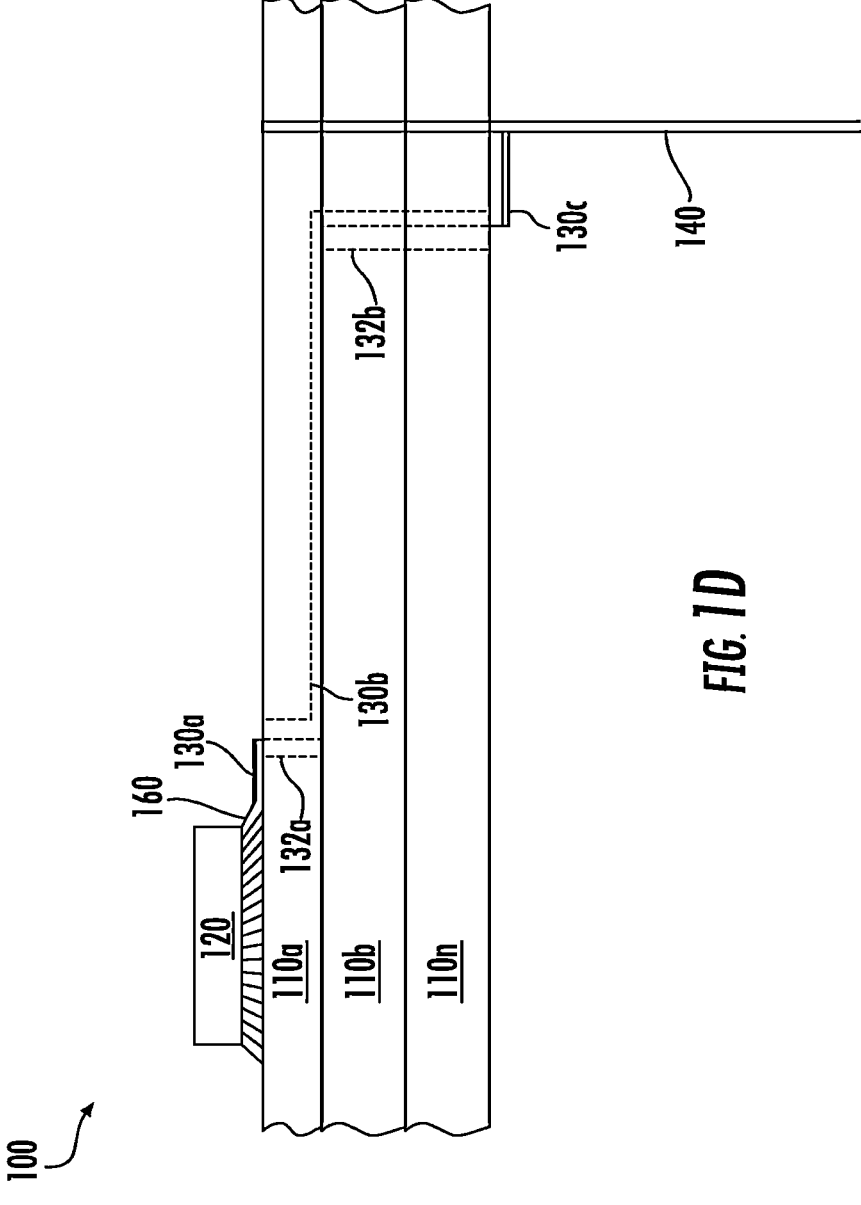
Figure 1E:
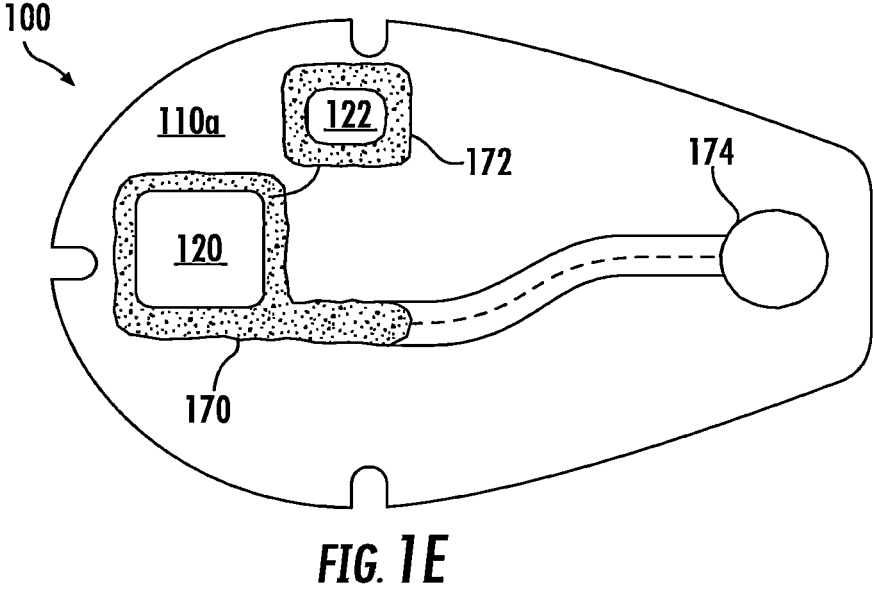
Figure 1F:
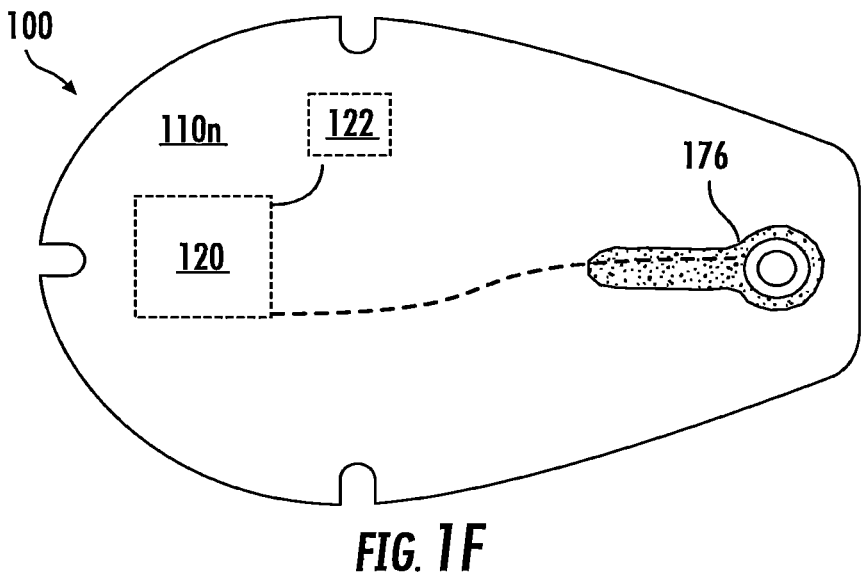

Referring now to FIGS. 1A-1F, FIGS. 1A-D show different views of an electronics portion of an example wearable device 100 having a moisture-resistant design, while FIGS. 1E-F shows the view of FIGS. 1A and 1C with a potting compound that is not shown in FIGS. 1A and 1C. In this example, the wearable device 100 is a CGM (also referred to as CGM 100), but may be any other suitable wearable device. For example, other wearable devices may include biosensors, such as blood oxygen sensors, electrocardiogram sensors, blood flow or pressure sensors, etc. In this example, the example CGM 100 is designed to have a low profile, e.g., less than approximately 9 mm. Thus, the height of electronics features constrains ways by which to prevent moisture damage to the electronics within the electronics portion of the CGM 100.

The electronics portion of the CGM 100 in this example includes a multi-layer PCB 110*a-n* to which are coupled a first semiconductor package 120; a second semiconductor package 122; a sensor wire 140; a sensor wire electrical trace 130*a-c*; and several guard rings 150*a-c*, 152*a-b*. It should be appreciated that other components may be included as well, or other electrical traces or electronic components to enable communications between different components or to provide other functionality. A multi-layer PCB is employed in some examples as interior layers of the PCB can provide moisture protection to electrical components, such as electrical traces, that are laid on such interior layers. For example, an electrical trace connecting a sensor wire to a semiconductor package that runs along an interior layer of the PCB may be protected from moisture by the other layers of the PCB. However, a multi-layer PCB is not required according to different examples.

FIG. 1A shows a top or upper layer 110*a* of the PCB and the components attached to it, as well as hashed lines indicating other identified components, which are present or coupled to other layers of the PCB. FIG. 1B shows an interior layer 110*b* of the PCB, while FIG. 1C shows the bottom or lowest layer 110*n* of the PCB. Layer 110*n* is referred to as the lowest or bottom layer because it is the layer that will be closest to a wearer's skin as the sensor wire last contacts the PCB at the lowest layer before extending away from the bottom layer and out of the CGM's housing such that it can be inserted into a wearer's skin. While in this example, the PCB has three layers, any suitable number of N layers may be employed. In this example, to reduce the overall height of the CGM 100, each layer 110*a-n* of the PCB has a thickness of approximately 0.020 inches (or 20 mils); however, PCB layers of any suitable thickness may be employed.

As can be seen in FIG. 1A, the semiconductor packages 120, 122 have a substantially rectangular shape with multiple pins that are coupled to the PCB. No requirement is imposed on the shape or number of pins of any semiconductor package; thus, other shapes or sizes may be employed as well. In this example, the package refers to the physical package within which integrated circuits may be encased, and the specifics of the integrated circuits may vary according to application. In this example, the first semiconductor package 120 has an integrated circuit, which is an ASIC that includes circuitry to receive signals from the sensor wire, determine a glucose level based on those signals, and to transmit information to the wireless transceiver. The second semiconductor package 122 also has an integrated circuit, which is a wireless transceiver in this example.

In addition to the semiconductor packages 120, 122, a sensor wire 140 is coupled to the PCB and is electrically connected to the ASIC 120 via an electrical trace 130*a-c*. As discussed above, by running a significant portion of the electrical trace 130*b* along an interior layer 110*b* of the PCB, most of the length of the sensor wire electrical trace 130*a-c* can be shielded from moisture by the exterior layers 110*a*, 110*n* of the PCB.

Referring to FIG. 1D, the sensor wire 140 is coupled to each of the layers 110*a-n* of the PCB and extends away from the lowest layer 110*n* of the PCB, thereby enabling the sensor wire 140 to be inserted into a wearer's skin. And while in this example, the sensor wire 140 extends through each layer 110*a-n* of the PCB, other configurations may be employed in some examples. For example, the sensor wire 140 may extend through only some, or even one, of the PCB layers 110*a-n*. In some examples, a portion of the sensor wire 140 may be soldered, grasped, or otherwise coupled to the lowest layer 110*n* of the PCB and another portion may bend and extend away from that layer 110*n*, e.g., at a 90 degree angle.

In this example, the sensor wire 140 has two electrodes that are inserted into a wearer's skin to expose the electrodes to the wearer's interstitial fluid, from which glucose readings may be taken. In this example, the two electrodes are (1) a platinum or platinum-coated wire, and (2) a silver/silver-chloride (Ag/AgCl) material that covers a part of the wire. One end of the sensor wire 140, including a portion of the Ag/AgCl material, extends downward from the bottom, or lowest layer 110*n*, of the PCB and may be inserted into the wearer's skin, while the other end of the sensor wire 140 is attached to the PCB.

In this example, a portion of the sensor wire 140 that is inserted into the wearer's skin also has a glucose oxidase ("GOX") coating that will react to glucose present within the wearer's interstitial fluid. When the sensor wire 140 is inserted into the wearer's skin, the GOX reacts with glucose, which creates reaction products, such as hydrogen peroxide. When a voltage is applied to the electrodes, an electrical current is generated based on the amount of these reaction products generated by the glucose/GOX reaction. The electrical current is then transmitted to the ASIC within the first semiconductor package 120 via the electrical trace 130*a-c*. The ASIC determines the amount of glucose that is present based on the strength of the current.

Because the example CGM 100 may be worn by a wearer for an extended period of time, such as days or weeks, it will likely be exposed to a variety of different environments, including water or high humidity environments as a result of the user bathing, swimming, etc. To help prevent damage to the CGM electronics, they are entirely disposed within a sealed housing. In addition, the electronics are protected from moisture by other aspects of the design, including routing electrical traces through interior portions of the PCB and using a potting compound on portions of the electronics and electrical traces.

For example, as can be seen in FIG. 1D, an electrical trace 130c couples to the sensor wire 140 on the lowest layer 110n of the PCB, traverses a short distance, e.g., 1-5 mm, before traversing a via 132b to an interior layer 110b of the PCB. The electrical trace 130b runs along the interior layer 110b to a second via 132a, which it to the top layer 110a of the PCB and couples to a pin 160 on the ASIC package 120. By routing the electrical trace 130b along an interior layer 110b of the PCB, that portion 130b of the electrical trace, plus the portions traversing the vias 132a-b, are protected from moisture that may enter the housing. Because the layers 110a-n of the PCB are bonded together and thus do not admit water between them. In addition, the vias 132a-b may be sealed when they are defined within the PCB, or the vias 132a-b may be filled with a potting compound to prevent ingress of moisture. It should be appreciated that while the example electrical trace 130a-c is illustrated as coupling the sensor wire 140 to the ASIC semiconductor package 120 without any intervening electronic components, in some examples, other electronic components may be coupled to the electrical trace 120a-c. Such as in one example, a resistor is coupled between the electrical trace 130a and the ASIC semiconductor package 120, which may provide electrical protection to electronics within the semiconductor package.

Referring now to FIGS. 1E-IF, portions of the electronics of FIGS. 1A-1D are shown protected by an encapsulant, such as a potting compound 170-176. Suitable encapsulants may be applied as a liquid or a gel during a manufacturing process, and may be cured at an elevated temperature. Such encapsulants should have a glass transition temperature above expected operational temperatures, including other manufacturing temperatures, e.g., related to forming a housing or welding portions of a housing together. In addition, the encapsulant should not be moisture sensitive and high electrical resistivity, e.g., greater than $10^{13}$ ohms per centimeter.

In this example, in addition to routing the electrical trace 130b along an interior layer 110b of the PCB, the portions of the electrical trace 130a and sensor wire 140 that are exposed on the top layer 110a, and the electrical trace 130c on the lowest layer 110-n are encased by a potting compound 170-176, which prevents moisture from reaching the otherwise exposed electrical traces 130a,c on the PCB. In examples where additional electronic components are provided along the route of the electrical trace 130a-c, e.g., the resistor discussed above, such components may also be encased in the potting compound 170 to ensure the exposed conductive path between the sensor wire 140 and the ASIC semiconductor package 120 is entirely encased by the potting compound 170, including the guard rings 150a-c, 152a-b, which are discussed in more detail below. In addition, in this example, the electrical traces 130a, c are first covered by a conformal coating, which may provide further moisture protection, and subsequently encased in a potting compound 170, 176; however, in some examples, a conformal coating is not employed.

It should be noted in this example that the sensor wire 140 extends away from the lowest layer 110n of the PCB to enable it to be inserted into a wearer's skin. Thus, a portion of the sensor wire 140 will also extend outside of the CGM's housing. Thus, the potting material 176 on the lowest layer is applied both to protect the exposed portions of the sensor wire 140 within the housing, but also to seal a hole in the housing through which the sensor wire 140 extends. Thus, the potting compound both encapsulates portions of the internal electronics of the CGM 100 but also serves as physical barrier by obstructing the hole traversed by the sensor wire 140. However, the potting material is not applied to the portions of the sensor wire 140 to be inserted into the wearer's skin.

In addition to encasing the electrical trace 130a-c in a potting compound, the pins of the semiconductor packages 120, 122 are also encased in the potting compound 170, 172. After the semiconductor packages 120, 122 have been coupled, e.g., soldered, to the top layer 110a of the PCB, the potting compound 170, 172 is applied around the perimeter of the semiconductor packages, thereby encasing the pins. However, the potting compound 170, 172 is not applied to the upper surface of the semiconductor packages. As discussed above, the CGM 100 is designed to achieve a low profile form factor. Applying a potting compound to the upper surface of the semiconductor packages 120, 122 would increase the respective heights of those components, potentially exceeding the desired profile, which in this example, again, is less than 9 mm.

In addition, as discussed above, the potting compound is only applied around the perimeter of the semiconductor packages 120, 122 and over the portions of the electrical trace 130a,c formed on the upper and lower layers 110a, 110n of the PCB and coupling the sensor wire 140 to the first electronics package. In some examples, the potting material may also be applied over one or more guard rings 150a-c, 152a-b. Thus, the potting compound does not add to the height of the tallest electronic components, e.g., semiconductor packages, affixed to the PCB, and does not affect the overall profile of the electronics portion of the CGM 100.

Suitable potting compounds according to this disclosure include materials having a glass transition temperature greater than 45 degrees Celsius, while having a cure temperature of less than 175 degrees Celsius. Such thermal characteristics may accommodate expected operating temperatures as well as temperatures that may be experienced during manufacture, e.g., resulting from contact with the wearer's skin or heat applied to weld portions of the housing together or to otherwise seal the CGM housing. In addition, suitable potting compounds have a resistivity of greater than $10^{13}$ ohms per centimeter, which may provide protection from short circuits for components encased in a common portion of the potting compound. Viscosity characteristics of suitable potting compounds include viscosities of approximately 800 poise (P) or greater; however, potting compounds having a variable viscosity during dispensing may improve manufacturing processes. One example suitable potting compound is Loctite® Eccobond® EO1072, also referred to as Hysol® EO1072, for which a technical data sheet is appended to this disclosure.

In addition to providing moisture resistance, the CGM electronics in this example include features to electrically isolate the sensor wire and the electrical trace that connects the sensor wire to the ASIC semiconductor package 120 from potential sources of current leakage. In this example, the CGM 100 employs a sensor wire 140 that, when inserted in a wearer's interstitial fluid, may provide a sensor signal with a current in the range of single-digit or tens of nanoamps ("nA"). Leakage of current from other electrical traces, ground planes, or electronic components onto the sensor wire 140 or its electrical trace 130a-c may interfere with the current generated by the sensor wire electrodes and thus may impact the accuracy of sensor readings or render them unusable. In this example, to electrically isolate the sensor wire 140 and its electrical trace 130*a-c*, multiple guard rings 150*a-c*, 152*a-b* are applied to the PCB and a physical configuration of a ground plane 180 corresponding to the ASIC semiconductor package 120 is shaped to help ensure the sensor wire and its electrical trace are protected from leakage current, as will be discussed in more detail with respect to FIG. 1G below.

Referring again to FIG. 1A, a portion of the sensor wire's electrical trace 130*a* runs along the top layer 110*a* of the PCB before traversing a via 132*a* to an interior layer as discussed above. In this example, a guard ring 150*a* encircles the portion of the electrical trace 130*a* on the top layer 110*a* of the PCB. By encircling the portion of the electrical trace 110*a*, current leaking from components near the electrical trace 130*a* may be absorbed by the guard ring 150*a*, and thus do not reach the electrical trace 130*a*. In addition, a guard ring 152*a* encircles the portion of the sensor wire 140 coupled to the top layer 110*a* of the PCB. Referring to FIG. 1B, the electrical trace 130*b* running along the interior layer 110*b* of the PCB is also encircled by a guard ring 150*b* formed on the interior layer 110*b* of the PCB. Similarly, a guard ring 152*b* encircles the portion of the sensor wire 140 coupled to the interior layer 110*a* of the PCB. It should be noted that if the PCB has more than three layers, guard rings may be formed on each of the interior layers to which the sensor wire has a connection, not merely those on which a portion of the electrical trace runs. Further, referring to FIG. 1C, the portion of the electrical trace 130*c* on the lowest layer 110*c* of the PCB is also encircled by a guard ring 150*c* as is the portion of the sensor wire 140 coupled to the lowest layer 110*c*. Thus, all portions of the sensor wire 140 coupled to the PCB layers, and the electrical trace 130*a-c* running from the sensor wire 140 to the ASIC semiconductor package 120 are encircled by guard rings 150*a-c*, 152*a-b*, thereby reducing the likelihood that leakage currents may reach the sensor wire 140 or the electrical trace 130*a-c* and affect the sensor signals.

Figure 1G:
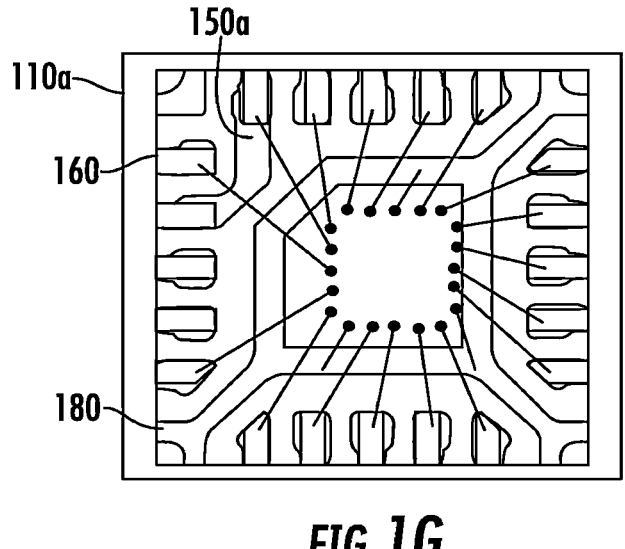

Referring now to FIG. 1G, FIG. 1G illustrates an example layout of a portion of the PCB corresponding to the ASIC semiconductor package 120. The layout defines multiple contact pads for the ASIC semiconductor package's pins as well as a ground plane 180 that couples to pins on three of the four corner portions of the package 120. However, the fourth corner portion lacks the corresponding ground plane conductor. Instead, a portion of the guard ring 150*a* couples two contact pads and provides an electrical barrier between the pin 160 that connects to the sensor wire's electrical trace 130*a* and the ground plane 180. Thus, while the semiconductor package 120 is provided with a ground plane 180, the sensor wire electrical trace 130*a* and the pin 160 on the ASIC semiconductor package 120 connected to the electrical trace 130*a* are encircled by a guard ring 150*a*, thereby shielding the electrical trace 130*a* and pin 160 from the ground plane 180.

Figure 1H:
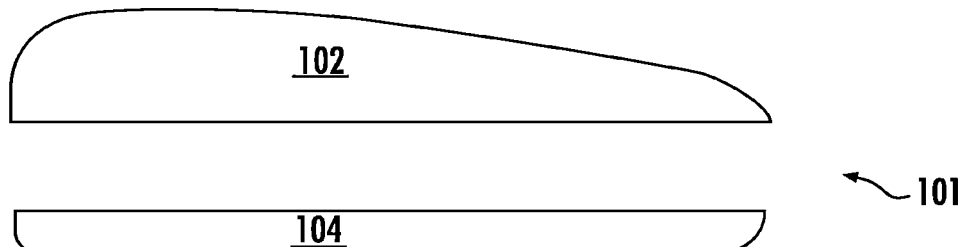
FIG. 1H-1I show views of an example housing for a CGM.
Figure 1I:
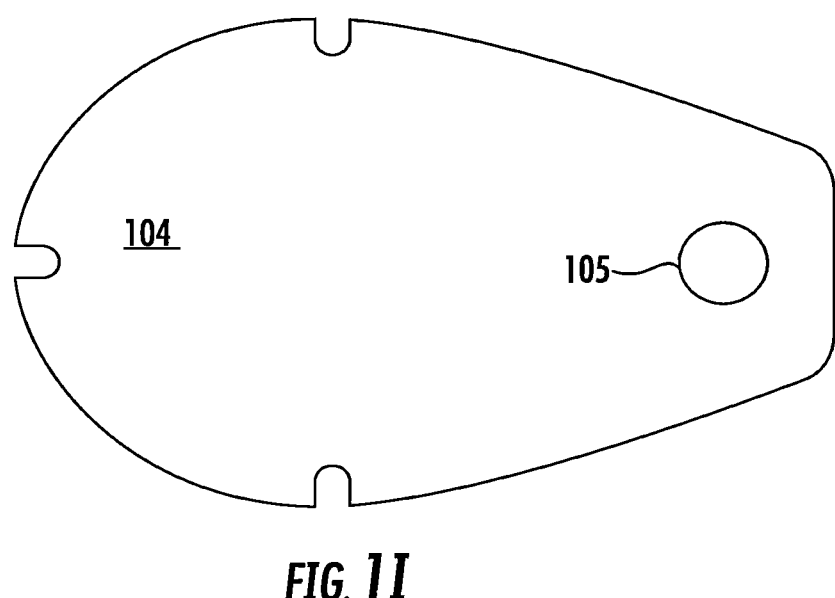

Referring now to FIGS. 1H-1I, FIGS. 1H-1I show an example housing 101 for the CGM 100 shown in FIGS. 1A-F. The housing 101 has an upper portion 102 and a lower portion 104 that can be coupled together, such as by an adhesive (e.g., an epoxy or resin) or via heat welding, to form a waterproof seal between the housing portions. In addition, the lower portion 104 of the housing defines a hole 105 through which the sensor wire 140 can pass. In this example, "lower" refers to the portion of the housing through which the sensor wire 140 passes. In addition, as discussed above, the hole 105 may be sealed with a potting compound after the sensor wire 140 has been inserted through the hold 105.

Example CGMs incorporating one or more of the aforementioned features may provide improved resistance to moisture or high-humidity environments, and may enable more accurate sensor readings by shielding the sensor electronics both from moisture and from leakage currents.

Figure 2:
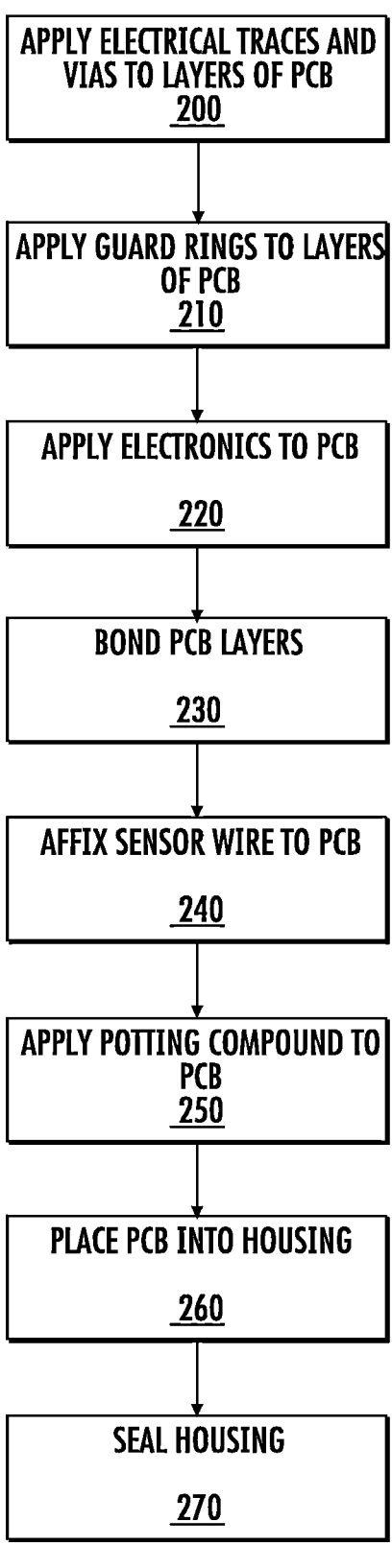
FIG. 2 shows an example method of providing a moisture-resistant CGM.

Referring now to FIG. 2, FIG. 2 shows an example method for providing an electrically-isolated and moistureresistant design for a wearable device. Discussion of the method shown in FIG. 2 will be made with respect to the example CGM 100 shown in FIG. 1; however, it should be appreciated that other example CGMs, or other types of electronic devices, may be provided according to examples methods according to this disclosure.

At block 200, electrical traces 130*a-c* are applied to the respective layers 110*a-n* of the PCB. In this example, the PCB will have three layers 110*a-n*, thus, before the layers 110*a-n* are bonded together, electrical trace 130*a* is applied to the first layer 110*a*, electrical trace 130*b* is applied to the second layer 110*b*, and electrical tracer 130*c* is applied to the third layer 110*n*. In addition, vias 132*a-b* are established in each of the layers 130*a-c* at locations corresponding to the ends of the respective traces 130*a-c* to provide a conductive path between layers 110*a-n*. While this example includes three PCB layers, any suitable number of layers, including 4 or more layers may be employed according to some examples.

At block 210, guard rings 150*a-c*, 152*a-b* are applied to one or more layers 110*a-n* of the PCB to encircle the electrical trace 130*a-c* corresponding to a sensor wire 140 on the respective layer. A guard ring in this example is formed by defining a trace entirely encircling an electrical trace on a respective layer, including any via through which the electrical trace runs. In some examples, the electrical trace may be applied to at least three layers of the PCB, and a guard ring may be applied to each of these layers and encircling the length of the electrical trace on the respective layer. In some examples, a guard ring may be omitted on one or more layers if no other electronic components or traces are routed or affixed to the layer.

At block 220, one or more electronic devices, such as semiconductor packages, resistors, capacitors, batteries, etc. are affixed to the appropriate layers of the PCB. For example, the semiconductor packages 120,122 may be soldered to corresponding bonding pads on top layer 110*a* of the PCB. In some examples, a resistor may be affixed to the top layer 110*a* of the PCB to couple the sensor wire electrical trace 130*a* to a pin 160 on the ASIC semiconductor package 120. In still other examples, fewer, additional, or different electronic devices may be affixed to layers of the PCB.

At block 230, the layers 110*a-n* are bonded together to create the multi-layer PCB. In this example, layer 110*b* is bonded between layers 110*a* and 110*n* after any electrical traces, guard rings, vias, or electrical components are applied or affixed to the layer 110*b*.

At block 240, a potting compound is applied to at least one of the top or bottom layers 110*a,n* of the PCB. In this example, a potting compound 170 is applied around the perimeter of the ASIC semiconductor package 120 that encases each of its pins. In addition, the potting compound 170 is applied over-top of the sensor wire electrical tracer 130*a* and the associated guard ring 150*a*. Potting compound 172, 174 is also applied around the perimeter of the wireless transceiver semiconductor package 122 and over-top of the sensor wire 140 coupled to the top layer 110*a* of the PCB. Potting compound 176 in this example is also applied to the bottom layer 110*n* of the PCB to encase the portion of the sensor wire electrical trace 130*c* and the guard ring 150*c* that encircles the electrical trace 130*c* and the sensor wire 140. It should be appreciated that a potting compound may not be applied to the bottom layer 110*n* of the PCB if the electrical trace coupling the sensor wire 140 to the ASIC semiconductor package 120 couples to the sensor wire on an interior layer 110*b* of the PCB. In such an example, potting compound is not applied to the interior layer 110*b* of the PCB.

At block 250, the sensor wire 140 is affixed to the PCB. In this example, the sensor wire 140 is inserted into a preformed hole in the PCB and soldered into place. However, in some examples, the sensor wire 140 may be soldered or affixed to the PCB, e.g., by one or more clamps or other features that provide an interference or frictional coupling. In some examples the sensor wire 140 may be bonded to the PCB using an adhesive, such as a non-conducting epoxy or resin.

At block 260, the PCB is disposed within a housing 101. In this example, the housing 101 is made of two housing portions, a lower portion 104 and an upper portion 102. The PCB may be disposed in a lower portion 104 of the housing 101 to allow the sensor wire 140 to extend downward through a corresponding hole 105 in the lower portion 104 of the housing 101. The upper portion 102 of the housing 101 may then be placed over the PCB and into contact with the lower portion 102 of the housing 101. And while, in this example, the housing 101 is made up of two portions 102, 104, other example housings may have more than two pieces, or may only have a single piece that entirely encases the PCB, or is open on one side, which may later be sealed, such as at block 270.

At block 270, the housing 101 is sealed. For example, the upper and lower portions 102, 104 of the housing 101 may be sealed using an adhesive, such as an epoxy or resin. In some examples, the upper and lower portions 102, 104 of the housing 101 may be heat welded together. In addition, a potting compound may be applied within the hole 105 in the lower portion 104 of the housing 101 after the sensor wire 140 has been inserted through it. The potting compound may provide a seal between the sensor wire 140 and the lower portion 104 of the housing 101 to provide a barrier against contaminants, such as moisture or dirt from entering the housing 101.

While the method of FIG. 2 has been described as having certain steps, in some examples, only some of the steps may be performed, or the steps may be performed in an order different than is described.

While some examples of methods and systems herein are described as having semiconductor packages that include circuitry. For example, a semiconductor package may include a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A wearable device comprising:
   a printed circuit board ("PCB") having first and second outer layers and an inner layer, the inner layer disposed between the first and second outer layers;
   a semiconductor package having a plurality of pins, the semiconductor package coupled to the first outer layer of the PCB via the plurality of pins;
   an electrical contact for a sensor formed on the second outer layer of the PCB;
   a sensor trace having a first portion disposed on the first outer layer, a second portion disposed on the inner layer, and a third portion disposed on the second outer layer;
   an encapsulant disposed around a perimeter of the semiconductor package, the encapsulant covering (i) the plurality of pins, and (ii) the first portion of the sensor trace, wherein the encapsulant is configured to not cover the sensor, and wherein an upper surface of the semiconductor package remains exposed.

2. The wearable device of claim 1, further comprising a housing defining a cavity and comprising a first housing portion and a second housing portion, the first housing portion coupled to the second housing portion to define the cavity.

3. The wearable device of claim 2, wherein the PCB is disposed between the first and second housing portions.

4. The wearable device of claim 2, wherein the first housing portion is welded to the second housing portion.

5. The wearable device of claim 2, wherein the second housing portion includes a first hole to allow the sensor to extend outside of the housing.

6. The wearable device of claim 5, wherein the PCB includes a second hole aligned with the first hole to allow the sensor to extend through the PCB.

7. The wearable device of claim 6, wherein the encapsulant is further disposed within the first hole and/or the second hole.

8. The wearable device of claim 1, wherein the sensor comprises first and second electrodes.

9. The wearable device of claim 1, wherein the encapsulant has a glass transition temperature greater than 45 degrees Celsius and a cure temperature of less than 175 degrees Celsius.

10. The wearable device of claim 1, wherein the encapsulant has a glass transition temperature greater than an operating temperature range of the wearable device and a cure temperature substantially lower than a melting temperature of a housing material of the wearable device.

11. The wearable device of claim 1, wherein the encapsulant has a resistivity of at least $10^{13}$ ohms per centimeter.

12. The wearable device of claim 1, wherein a total height of the PCB and the semiconductor package is less than 9 millimeters.

* * * * *